United States Patent [19]

Siskin et al.

[11] 4,094,924

[45] June 13, 1978

[54] PROCESS FOR THE ALKYLATION OF LIGHT PARAFFINS WITH LOWER OLEFINS

[75] Inventors: Michael Siskin, Maplewood; Ivan Mayer, Summit, both of N.J.

[73] Assignee: Exxon Research & Engineering Co., Linden, N.J.

[21] Appl. No.: 816,801

[22] Filed: Jul. 18, 1977

Related U.S. Application Data

[63] Continuation-in-part of Ser. No. 586,591, Jun. 13, 1975, abandoned.

[51] Int. Cl.² .................................................. C07C 3/54
[52] U.S. Cl. ........................... 260/683.51; 260/683.47
[58] Field of Search ..................... 260/683.47, 683.51, 260/683.58, 683.53

[56] References Cited

U.S. PATENT DOCUMENTS

| | | | |
|---|---|---|---|
| 2,342,865 | 2/1944 | Ipatieff et al. | 260/683.47 |
| 2,355,339 | 8/1944 | Story | 260/683.53 |
| 2,470,144 | 5/1949 | Clark | 260/683.47 |
| 3,678,120 | 7/1972 | Bloch | 260/683.47 |
| 3,708,553 | 1/1973 | Olah | 260/683.47 |
| 3,778,489 | 12/1973 | Parker et al. | 260/683.47 |
| 3,852,371 | 12/1974 | Kemp | 260/683.47 |
| 3,979,476 | 9/1976 | Kemp | 260/683.47 |
| 4,025,577 | 5/1977 | Siskin et al. | 260/683.47 |

OTHER PUBLICATIONS

Noller, Carl R. "Chemistry of Organic Compounds", W. B. Saunders Co., Philadelphia, (1966), Chapter 6, p. 111.

Siskin, Michael "Alkene-Alkane Alkylations in HF—TaF₅" Journal of ACS, vol. 98, pp. 5413–5414, (1976).

*Primary Examiner*—George Crasanakis
*Attorney, Agent, or Firm*—John W. Ditsler

[57] ABSTRACT

Alkylates are prepared by selectively alkylating light paraffinic hydrocarbons with lower olefins at alkylation conditions in the presence of a catalyst comprising (a) one or more Lewis acids of the formula $MX_n$ where M is selected from the Group IIIA, V or VIB elements of the Periodic Table, X is a halogen, $n$ is the ratio of halogen atoms to atoms of M and varies from 1–8, and (b) a hydrogen halide.

28 Claims, No Drawings

PROCESS FOR THE ALKYLATION OF LIGHT PARAFFINS WITH LOWER OLEFINS

CROSS REFERENCE TO RELATED APPLICATIONS

This is a continuation-in-part of application Ser. No. 586,591, filed June, 13, 1975 and now abandoned.

BACKGROUND OF THE INVENTION

The present invention relates to a process for the selective alkylation of light paraffinic hydrocarbons with lower olefins in the presence of a catalyst comprising (a) one or more Lewis acids of the formula $MX_n$ where M is selected from Group IIIA, V or VIB elements of the Periodic Table, X is a halogen, n is the ratio of a halogen atoms to atoms of M and varies from 1-8, and (b) a hydrogen halide. The preferred Lewis acid is a metal halide, preferably tantalum pentafluoride, niobium pentafluoride or mixtures thereof. The preferred hydrogen halide is hydrogen fluoride.

DESCRIPTION OF THE PRIOR ART

The acid catalyzed addition of an alkane to an alkene is well known in the art. Generally, the catalytic alkylation of paraffins involves the addition of an alkyl cation derived from an isoparaffin containing a tertiary hydrogen to an olefin. The process is used by the petroleum industry to prepare highly branched $C_6$–$C_9$ paraffins that are high quality fuels for internal combustion and other engines. The process conditions required and the product composition depend on the particular hydrocarbons involved in the reaction.

The most important rate-determining factor in the alkylation reaction is the hydride abstraction step; i.e. the removal of a hydride ion from the isoparaffin to form an alkyl cation. In the case of isoparaffins, such as isobutane, the conversion to the cation is fairly rapid even at low temperatures, e.g., $-10°$ to $40°$ C. However, in the case of normal paraffins such as normal butane, the formation of the alkyl cation, with the generally known catalyst systems, proceeds very slowly at ordinary alkylation temperatures.

Hydrocarbon conversion processes involving the use of metal halide based catalysts have been extensively described in the prior art. For example, U.S. Pat. Nos. 2,683,763 and 2,683,764 disclose that tantalum pentafluoride or columbium (niobium) pentafluoride in combination with hydrogen fluoride can be used to refine hydrocarbon oils or to promote the disproportionation of alkyl-substituted aromatic materials. The patentees also disclose that hydrogen fluoride/tantalum pentafluoride are powerful catalysts for isomerization, alkylation, cracking and other reactions of aromatics. More recently, U.S. Pat. No. 3,708,553 teaches that high octane alkylates can be produced by contacting paraffinic and/or alkyl substituted aromatic hydrocarbons with olefins in the presence of a catalyst comprising one or more metal halides and a strong Bronsted acid selected from the group consisting of fluorosulfuric acid and trifluoromethanesulfonic acid and mixtures thereof. However, when paraffinic hydrocarbons are selectively alkylated with another paraffin or an olefin in the presence of hydrogen using the catalyst system of the present invention as described hereinafter, there will result in alkylate of enhanced product quality because of better selectivity than that obtained using catalyst systems taught in the prior art.

SUMMARY OF THE INVENTION

Now in accordance with the present invention, it has been discovered that normal paraffinic hydrocarbons selected from the group consisting of methane, ethane, propane, n-butane and mixtures thereof, are selectively alkylated with lower olefins, preferably ethylene, propylene or mixtures thereof, at alkylation conditions in the presence of a catalyst comprising (a) one or more Lewis acids of the formula $MX_n$ where M is selected from the Group IIIA, V, or VIB elements of the Periodic Table, X is a halogen, preferably fluorine, n is the ratio of halogen atoms to atoms of M and varies from 1-8, and (b) a hydrogen halide, preferably hydrogen fluoride. In general, reaction temperatures may range from about $-100°$ to about $+150°$ C, preferably from about $-30°$ to about $+100°$ C and more preferably from about $-10°$ to about $+80°$ C.

Catalysts of the type described herein have been well known to catalyze alkylation reactions, particularly where the second component is fluorosulfuric acid or trifluoromethanesulfonic acid. It has been surprisingly found, however, that when a hydrogen halide, preferably hydrogen fluoride, is employed in conjunction with a metal halide, preferably tantalum pentafluoride, niobium pentafluoride or mixtures thereof, the reaction is highly selective to the formation of desirable alkylate products. Thus according to the present invention, selectivity to $C_3$ and $C_4$–$C_8$ branched alkylate product is enhanced because the formation of intermediate esters and subsequent polymerization reactions which occur when using either fluorosulfuric acid or trifluoromethanesulfonic acid under similar reaction conditions is minimized. Preferably, the present alkylation process is conducted in the substantial absence of aromatic compounds.

DETAILED DESCRIPTION OF THE INVENTION

The hydrocarbon conversion catalyst referred to herein comprises one or more Lewis acids of the formula $MX_n$ where M is selected from the Group IIIA, V, or VIB elements of the Periodic Table, X is a halogen, preferably fluorine, n is the ratio of halogen atoms to atoms of M and varies from 1-8, and (b) a hydrogen halide. The Periodic Table referred to is that described in "The Encyclopedia of Chemistry", Reinhold Publishing Corporation, 2nd Ed. (1966) at page 790. The terms "elements" as used herein refers to the metals and metalloids of the aforementioned Groups of the Periodic Table.

One component of the catalyst system is one or more Lewis acids. Metal halides are preferred Lewis acids. Useful metal halide constituents include the fluorides, bromides and chlorides of vanadium, niobium, tantalum, chromium, molybdenum, tungsten, arsenic, antimony, bismuth and the chlorides and bromides of gallium and aluminum. Group V and VIB metal fluorides are preferred metal halides, Group V being more preferred, Group VB being most preferred. Specific examples of useful metal fluorides include antimony pentafluoride, tantalum pentafluoride, niobium pentafluoride, vanadium pentafluoride, tungsten hexafluoride, molybdenum hexafluoride, bismuth pentafluoride, arsenic pentafluoride, mixtures thereof and the like. The fluorides, chlorides and bromides of phosphorus, particularly phosphorus pentafluoride, are also suitable Lewis acids. The most preferred metal halide catalyst constituents are tantalum and niobium halides, preferably tantalum pentafluoride, niobium pentafluoride and mixtures thereof. Tantalum pentafluoride is meant to include tantalum pentafluoride as well as other fluoride species, e.g. ions such as $Ta_2F_{11}^-$, $Ta_3F_{16}^-$ and the like, they may be formed when tantalum pentafluoride is mixed with the hydrogen halide, alone or in combination with the feedstock. This applies similarly to other metal halides.

The second component of the catalyst system is a hydrogen halide. Useful hydrogen halides include hydrogen bromide, hydrogen chloride, and hydrogen fluoride. The preferred hydrogen halide catalyst constituent is hydrogen fluoride. The hydrogen halide should be chosen so as to avoid unfavorable exchange reactions with the Lewis acid. For example, the fluoride in hydrogen fluoride will displace the bromide or chloride in a metal halide to form the metal fluoride and the corresponding hydrogen halide. Thus, hydrogen fluoride should be used with only metal fluorides. Similarly, hydrogen bromide can be used with metal fluorides, chlorides or bromides.

According to the present invention, applicants have found that the selectivity to $C_3$-$nC_4$ and $C_4$-$C_8$ branched alkylate is enhanced by use of a hydrogen halide, rather than other acids such as fluorosulfuric and trifluoromethanesulfonic, in combination with a metal halide. This is due primarily to minimizing the formation of intermediate esters, polymerization reactions and the like. While not wishing to be bound by any particular theory, applicants believe that such undesirable reactions are minimized because sulfonic acid ester formation does not occur in the presence of a hydrogen halide. As such, acid dilution and consumption due to concomitant sludge, polymerization reactions, etc; i.e. reactions which lead to catalyst degradation, poorer product quality, and excessive consumption of the hydrocarbon feedstock, are minimized. Another factor which is believed to contribute to the higher selectivity to $C_3$-$nC_4$ and $C_4$-$C_8$ branched alkylate with the present hydrogen halide containing acid systems is the lower solubility of the unsaturated organic materials, e.g. olefins, in the above-mentioned non-oxygenated acids.

It has also been discovered that the present alkylation process is more efficient when carried out in the substantial absence of aromatic compounds. In the present invention, the aromatic compounds can be alkylated to more basic compounds which in turn will dilute the acid catalyst and hence the effectiveness of the catalyst. Thus, although aromatic compounds may be present in the feedstock, it is preferred that the present alkylation process be conducted in their substantial absence, i.e. less than about 1 wt. %, preferably less than 0.1 wt. %.

The effectiveness of the catalyst is related to the molar ratio of hydrogen halide to Lewis acid. While relatively minor amounts, i.e. less than equimolar amounts, of hydrogen halide relative to Lewis acid will dissolve at least a portion of the Lewis acid and thereby effect the reaction, the rate of reaction is inordinately slow. However, the reaction rate, i.e. the yield in a given period of time, will be increased if at least an equal molar amount of hydrogen halide relative to Lewis acid is present in the reaction zone. Increasing the mole ratio of hydrogen halide to Lewis acid provides additional hydrogen halide so as to dissolve more of the Lewis acid and thereby provide an increasing amount of liquid phase catalyst which will favor an increased reaction rate. The effect of increasing amounts of liquid phase catalyst on reaction rate becomes more pronounced when the mole ratio of hydrogen fluoride to Lewis acid is in excess of one and continues as the liquid phase of the catalyst increases. Thus, the mole ratio of hydrogen halide to Lewis acid (metal halide) is preferably at least 2:1 and more preferably at least 5:1. The favorable effects mentioned above will pass through a maximum as the hydrogen halide dilutes the acidity of the reaction system. Thus, it is desirable that the molar ratio of hydrogen to Lewis acid be maintained below about 100:1 (i.e., between 1:1 and about 100:1), preferably between 1:1 and about 75:1, more preferably between 2:1 and about 75:1 and most preferably between 5:1 and about 50:1. Depending upon the relative amounts of catalyst constituents used, the catalyst, when no support is employed, may be a homogeneous solution of the metal halide in the hydrogen halide or a mixture of solid and dissolved metal halide in hydrogen halide.

The amounts of the aforementioned catalyst present during alkylation is not critical to the practice of the present invention. In general, the catalyst is employed in catalytic amounts. For operations with a liquid catalyst or with a liquid catalyst comprising a slurry of solid catalyst in liquid catalyst, the olefin to catalyst concentration must be maintained at a low level to minimize polymerization and sludge formation while simultaneously promoting the preferred alkylation reactions. Thus, at the point of olefin introduction, the olefin concentration on catalyst must be maintained at a low level, i.e. the amount of olefin introduced per unit time relative to the catalyst moving past the point of olefin introduction must be maintained at a low level. Therefore, the amount of olefin contacted with the catalyst can range from about 0.0001 to 0.05 parts by volume of olefin per part by volume of catalyst passing the point of olefin introduction. Preferably, the amount of olefin present will range from 0.0005 to 0.005 parts by volume per part by volume of the catalyst present at the point of olefin feed introduction. In addition, the volume percent of catalyst in the emulsion mixture, i.e., the liquid hydrocarbon plus catalyst, ranges from about 30 to about 85, preferably from about 50 to about 70.

The catalyst may be used as the neat liquid, as a diluted solution or as a solid, such as adsorbed on a solid support. If on a support, the catalyst may be used in a fluidized bed, in a molten salt process or suspended in a reaction mixture. With regard to the use of the catalyst in a solution, any diluent or solvent may be used that is inert to the catalyst under the particular hydrocarbon conversion reaction conditions. To obtain optimum results, the diluents should be pretreated to remove catalyst poisons such as water and the like. Typical diluents or solvents include sulfuryl chloride fluoride, sulfuryl fluoride, sulfolanes, fluorinated hydrocarbons, Freons, polyfluorinated-polyhalogenated hydrocarbons, mixtures thereof, and the like. Hydrogen fluoride is the preferred catalyst diluent when the Lewis acid portion of the catalyst system is a metal fluoride. When a solvent or diluent is used, sufficient amounts are employed to maintain the viscosity of the catalyst mixture at a desired level. The amount of diluent employed can vary appreciably and can range as high as 98 volume % of the catalyst mixture. Preferably, the diluent catalyst volume ratio may range from about 20:1 to 1:1. Higher dilutions may be desirable, for example, in those reactions that proceed with high exothermicity.

The catalyst may be mixed in the absence of any diluent. The components of the catalyst can be mixed separately, that is preferably in the absence of reactants, or in situ in the presence of reactants. In general, the order in which the reactants are added is not critical, thereby permitting a variety of procedures to be used.

The catalyst system may be employed with a suitable solid carrier or support. Any solid catalyst support may be used that is inert to the catalyst under the reaction conditions. If the support is not inert, the support should be pretreated, such as by heating, chemical treatment or coating, to remove substantially all water and/or hydroxylic sites that might be present. Reactive supports may be rendered inert by coating them with an inert material such as antimony trifluoride or aluminum trifluoride or by treatment with Freons, fluorine, or fluorinating agents such as when hydrogen fluoride is present in the catalyst. Suitable solid supports include fluoride-treated or coated resins such as sulfonated cation exchange resins, fluoride-treated acidic chalcites such as alumina and aluminosilicates and acid-resistant molecular sieves such as faujasite and zeolites, graphite, chromosorb T, Fluoropak 80, etc.

The supported catalyst can be prepared in any suitable manner, such as by conventional methods including dry mixing, coprecipitation or impregnation. In one embodiment, the supported catalyst is prepared by impregnating a suitable deactivated support with a Lewis acid such as tantalum pentafluoride and then with a hydrogen halide such as hydrogen fluoride. The weight ratio of the Lewis acid and hydrogen halide to the support can range from 1:100 to 1:10.

Olefins containing 2 to 5 carbon atoms per molecule are suitable for use in the present invention while olefins containing 2 and 3 carbon atoms per molecule are particularly preferred. However, it should be pointed out that while the thermodynamics of the reaction between $C_4$ and/or $C_5$ olefins with $C_1$–$nC_4$ paraffins is favorable, it is believed that said olefins will be protonated to form tertiary cations which may not react with said paraffins. Therefore, the scope of the present invention covers the use of $C_4$ and/or $C_5$ olefins to the extent that they will react with the $C_1$–$nC_4$ paraffins.

The reaction mixtures may also contain some amounts of diolefins. Although it is desirable from an economic viewpoint to use the normally gaseous olefins as reactants, normally liquid olefins may also be used. The use of two or more of the above-described olefins is also envisioned for use in the present process. Paraffinic hydrocarbon feedstocks that are suitable for use in the present process are the normal light paraffins, namely methane, ethane, propane and normal butane.

The present catalyst systems are particularly suited for use in refinery alkylation processes. The process of this invention contemplates the use of various refinery streams as feedstocks. Thus, $C_2$, $C_3$, and $nC_4$ cuts from thermal and/or catalytic cracking units; field butanes which need not have been subjected to prior isomerization; refinery stabilizer bottoms; spent gases; normally gaseous products from sulfuric acid or phosphoric acid catalyzed polymerization and copolymerization processes; and products, normally gaseous in character, from thermal and/or catalytic cracking units, are all excellent feedstocks for the present process. Such feeds are preferably dried to control excess water buildup, i.e. about 0.5 to 15 wppm, preferably 0.5 to 2 wppm, of water before entering the reaction zone.

The molar ratio of olefin to paraffin in the feed may range from 1:1 to 1:200, preferably from 1:3 to 1:50 and more preferably from 1:5 to 1:25. In general, a high dilution of the olefin is preferred in order to prevent competitive side reactions such as olefin polymerization and sludge forming reactions. In addition, the concentration of olefins dispersed in the acid should be low to allow substantially all of the olefin to be protonated. Thus, preferred operations are at low olefin feed rates relative to catalyst inventory, i.e., at low olefin space velocity.

The feed may also contain various cracking inhibitors or moderators such as hydrogen. The inhibitors act to accelerate cleavage reactions, which result from polymerization that may occur during the alkylation. When such reactions do occur, the hydrogen facilitates the hydrocracking of these polymers. Hydrogen is the preferred moderator when processing lower paraffins and lower olefins and may be used in amounts ranging from about 0.1 to 5 weight % or more based on hydrocarbon feed. Hydrogen, if present, may be in the form of hydrogen-containing gas, i.e., a gas containing molecular hydrogen. The gas may be obtained from any number of sources including commercially available pure hydrogen, naphtha reformers, hydrogen plants, as well as the off gases from any hydrotreating process or hydrogen donor organic molecules such as tetralin, methylcyclohexane, decalin, isobutane and the like. The term hydrotreating process is meant to include hydrofining, hydrocracking, hydrodesulfurization and the like or synthetic schemes in which hydrogen is a product. The hydrogen-containing gas may be pure or contain other gaseous materials such as light hydrocarbons ($C_1$–$C_8$), carbon dioxide, hydrogen sulfide and the like. Depending upon the nature of the feedstock and the alkylation conditions, some of the $C_1$–$C_8$ light hydrocarbons will alkylate to form additional product. The hydrogen-containing gas may be introduced into the alkylation process alone or be mixed with the hydrocarbon feed prior to said introduction. Preferably the hydrogen-containing gas will be dry.

The catalyst system employed herein are quite sensitive to impurities such as water and water-forming compounds, e.g. alcohols, ethers and such oxygen-containing compounds. Therefore the present alkylation process should be conducted in the absence of large amounts of moisture, and preferably under substantially anhydrous conditions, i.e. less than 1 wt. %, preferably less than 0.5 wt. % water, based on Lewis acid component of the catalyst. The water concentration on catalyst can be maintained at the desired level by continuous or batch replacement of water laden catalyst with substantially water-free catalyst.

In general, the alkylation reaction temperatures will vary in the range of from about −100° to about +150° C., preferably from about −30° to about +100° C., more preferably from about −10° to about +80° C. The pressure at which the reaction is carried out will depend upon the feed stream being processed, the reaction diluent, as well as other process variables. In general, the pressure should be sufficient to maintain at least a portion of one of the catalyst components in the liquid phase. Preferably, the present alkylation process will be conducted with the catalyst substantially in the liquid phase when using an unsupported catalyst system. The paraffin feed may or may not be in the liquid phase depending upon the particular paraffin as well as the temperature and pressure employed. If hydrogen is present, this may be expressed in terms of hydrogen partial pressure which should be at least 0.1 atmospheres and may range from about 0.1 to about 75 atmospheres, preferably from about 0.3 to about 25 atmospheres. The total pressure may range from about 1.0 to about 150 atmospheres. The present alkylation process may be conducted in the presence of an inert atmosphere, such as nitrogen. It is preferred that said alkylation be conducted in the substantial absence of an oxygen-containing gas, i.e. less than 1 wt. percent oxygen based on the inert atmosphere.

The olefins and paraffins are contacted in the presence of a catalyst for a time sufficient to effect the degree of alkylation desired. In general, the contact time is subject to wide variation. The length of the contact time depends in part upon the temperature, the olefin used and the catalyst concentration employed. Typical contact times will range from about 0.05 seconds to several hours, preferably from about 0.05 seconds to about 1 hour, more preferably from the 0.05 seconds to about 45 minutes. The amount of catalyst employed for carrying out the present invention can vary appreciably such, that in general, the volumetric space velocity, based on the olefin, will range from about 0.01 to about 1 V/Hr./V, preferably from about 0.04 to about 0.2 V/Hr./V (liquid volume or pseudo liquid volume olefin per hour per volume of catalyst. By pseudo liquid volume is meant the volume a gas would have if it were liquid at 60° F.).

The alkylation process of the present invention may be conducted in a batch, intermittent or continuous type operation. Preferably, the invention is carried out in a continuous manner to minimize further reaction of the product or products formed. It has been generally established that in alkylation processes, the more intimate the contact between the feedstock and the catalyst the better the yield of saturated product obtained. Thus, the apparatus employed may be of a conventional nature and may comprise a single reactor or multiple reactors equipped with efficient stirring devices such as mechanical agitators, turbomixers, jet mixers, and the like. One or more reactants may be introduced into the reaction zone through dispersion devices such as jets of restricted internal diameter, porous thimbles, and the like. The hydrocarbon paraffin-olefin phase, the catalyst phase and the hydrogen-containing gas, if present, may be passed through one or more reactors in cocurrent, cross-current, or counter-current flow. After a sufficient period of time, unreacted reactants, partially deactivated catalyst, inhibitors and heavier products of the reaction may be separated from the desired alkylation product and from one another, such as by distillation, and returned in whole or in part to the alkylation zone. If desired, a portion of the partially deactivated catalyst can be regenerated or reactivated by any suitable treatment and returned to the alkylation process.

As in other alkylation processes, more accurate control of the quality of the final product may be obtained if the reaction system is provided with a recycling feature wherein the unconverted hydrocarbons are mixed with fresh feed and returned to the feed dispersion device in the reaction zone.

Reactions involving the use of the present catalyst systems can be conducted in vessels fabricated from carbon steel provided that excessive temperatures are not used and provided further that the reaction system is maintained in a substantially anhydrous condition. Carpenter 20 Cb-3 (Alloy 20) Steel, Monel or Hastelloy C may also be used in the fabrication of reaction equipment as well as aluminum-magnesium alloys, e.g., aluminum 5052, 6061, and the like.

In general, reaction and/or recovery schemes and apparatus employed in conjunction with prior art liquid acid catalyst systems can be used with the catalyst systems of the present invention. Examples of potentially applicable process techniques and apparatus are described in U.S. Pat. Nos. 2,433,944, 2,479,366, 2,701,184, 2,717,913, 2,775,636, and 3,766,293, U.K. Pat. Nos. 543,046, 577,869, 731,806, 738,348, 803,458, 804,966, and 881,892, the disclosures of which are incorporated herein by reference.

Thus by following the method of the present invention, lower paraffins such as methane, ethane, propane and normal butane can be catalytically alkylated in an alkylation zone by $C_2$-$C_5$ olefins, particularly ethylene and propylene. Preferably, the hydrocarbon feedstock comprises methane, ethane, propane or mixtures thereof; more preferably methane or ethane or mixtures thereof; and most preferably methane. For example, methane, ethane, propane and n-butane can be reacted with ethylene to form propane, butane, pentanes and hexanes, respectively. Similarly, methane, ethane, propane and n-butane can be reacted with propylene to form isobutane, pentanes, hexanes, and heptanes, respectively. If desired, the paraffins, e.g. propane and butanes, so formed may undergo further alkylation with ethylene and/or propylene to produce additional higher molecular weight paraffins, e.g., pentanes, hexanes and heptanes. This further alkylation may be preferred if the objective of the process is increased liquid product.

Alternatively, the paraffins so formed may be further contacted with the catalyst in the alkylation zone for a period of time sufficient to form an olefin having the same number of carbon atoms as the corresponding paraffin, e.g. propylene is formed from propane. However, one molecule of a lower olefin, e.g. ethylene, present in the alkylation zone will be consumed and converted to its corresponding paraffin during the conversion of propane to propylene. The olefin thus formed (propylene) may be removed from the reaction zone or be allowed to undergo further alkylation with $C_1$-$C_4$ normal paraffins to form higher molecular weight paraffins as above, e.g. propylene may react with ethane to form isopentane. This additional contacting of the paraffin with the catalyst to make propylene may be preferred if the olefin is the desired product.

The process of the present invention is particularly advantageous to the petroleum industry. One advantage is that the liquid hydrocarbon product so formed may be suitably used as gasoline blending components. Another advantage is that natural gas can be processed directly at refineries located near sources of said gas, thereby increasing the yield of liquid product. Yet another advantage is that the present invention provides for the production of fuels such as propane and/or butane. Still another advantage is that both fresh and recycle feeds to a catalytic cracker, which contain considerable olefinic materials and are thus hydrogen deficient, can be reacted with methane instead of costly hydrogen to increase the low hydrogen to carbon ratio associated with said feeds.

The following examples are presented to further illustrate the process and advantages of the present invention and are not intended to unduly restrict the limits of the claims appended hereto:

EXAMPLE 1 — REACTION OF METHANE AND ETHYLENE WITH TaF$_5$/HF

Into a 300 ml Hastelloy C Autoclave Engineer's stirred autoclave were placed tantalum pentafluoride (55.2 g, 0.20 mole) and hydrogen fluoride (39.56 g, 1.98 mole). The catalyst was heated to 40° C. and pressurized to 150 psig with methane. Ethylene (70 psig in a 500 cc stainless steel high pressure cylinder) was then added slowly over a three hour period and the temperature was not allowed to increase more than about 2° C. by circulating cooling water through coils within the reactor. At the end of the ethylene addition, an acid sample (~2 cc) was taken and quenched in cold caustic. A gas sample was taken from a system installed in the exit line of the reactor and analyzed on a Perkin Elmer Model 900 Gas Chromatograph using an 18 ft. long silica gel - 10 ft. DC-200 column connected in series and a flame ionization detector. Analysis of the reaction mixture indicated that 33% of the ethylene was recovered with the only major product being propane with 42% selectivity, i.e. 42% of the product, excluding reactants, was propane. Higher boiling products resulting from degradation by ethylene polymerization amounted to only 3.65% of the total ethylene added based on analysis of the acid sample.

EXAMPLE 2 — REACTION OF METHANE AND ETHYLENE WITH TaF$_5$/HF.

A methane-ethylene (85.9 wt. %/14.1 wt. %) gas mixture was passed continuously at a rate of 42 standard cubic centimeters per minute through the autoclave of Example 1, which contained 50 cubic centimeters of hydrogen fluoride (2.0 mole) and tantalum pentafluoride (0.2 mole). The system was stirred at 100 rpm and maintained at 40° C., the temperature not being allowed to vary by more than about 1° C. After both 1.5 and 2.5 hours of continuous flow, the reaction product was analyzed as before and found to have about 58 wt. % selectively to propane.

EXAMPLE 3 — REACTION OF METHANE AND ETHYLENE WITH TaF$_5$/HF

Using the procedure and reaction conditions of Example 2, ethylene (~15 wt. %) diluted with helium was reacted. After about 40 minutes, a sample of the reaction product was taken and analyzed as before. The results showed that no propane product had been formed indicating that the desired product was being made via alkylation (as shown in Examples 1, 2, 4-8) rather than from ethylene or degradation of polymerized ethylene.

EXAMPLE 4 — REACTION OF ETHANE AND ETHYLENE WITH TaF$_5$/HF.

Using the procedure and reaction conditions of Example 2, an ethane/ethylene gas mixture (82.1 wt. %/17.9 wt. %) was reacted. After about 15 minutes, samples of the reaction product were collected and analyzed as before. The results indicated that normal butane comprised 77-81 wt. % of the product excluding reactants.

EXAMPLE 5 — REACTION OF n-BUTANE AND ETHYLENE WITH TaF$_5$/HF.

Using the procedure and reaction conditions of Example 2, a normal-butane solvent (83.9 wt. %) was contacted with ethylene (14.1 wt. %) which was introduced gradually into the pressurized reactor. After 1.5 hours, a sample of the reaction product was taken and analyzed as before. The results showed that a mixture of methylpentanes, e.g. paraffinic hexanes, which were formed by the rapid isomerization of the methylpentanes to an equilibrium distribution, were formed with 95% selectivity excluding reactants.

EXAMPLE 6 — REACTION OF METHANE AND ETHYLENE WITH TaF$_5$/HSO$_3$F.

Using the procedure and reaction conditions of Example 2, a methane-ethylene gas mixture (~85 wt. %/15 wt. %) was contacted with a catalyst composed of tantalum pentafluoride (27.1 g, 0.1 mole) and fluorosulfonic acid (100.0 g, 1.00 mole). The propane yield during 1-½ hours of reaction was found to be between 0.1-0.2% of the gas phase reaction mixture and the ethylene concentration varied from 0.1 to 1.9 wt. % of the gas phase reaction mixture. When hydrogen fluoride was used as a catalyst component, the ethylene content of the gas phase was typically between 30-60%. This indicates that when fluorosulfuric acid is a component of the catalyst system, ethylene is absorbed into the acid layer where it undergoes undesirable alkylation-polymerization reactions. The lower reactivity of the olefin to polymerization in hydrogen fluoride systems permits the alkylation reaction to proceed with greater selectivity than the competing polymerization reactions.

EXAMPLE 7 — REACTION OF METHANE AND ETHYLENE WITH SbF$_5$/HSO$_3$F.

Using the procedure and reaction conditions of Example 2, a gas mixture of methane and ethylene (~80 wt. %/20 wt. %) was contacted with a catalyst composed of antimony pentafluoride (21.7 g, 0.10 mole) and fluorosulfuric acid (100.0 g, 1.00 mole). The amount of propane found was almost identical with that described in Example 6, except that 2.5-4.2 wt. % ethylene was observed in the gas phase product.

EXAMPLE 8 — REACTION OF METHANE AND ETHYLENE WITH TaF$_5$/CF$_3$SO$_3$H.

Example 2 was repeated using a catalyst composed of tantalum pentafluoride (27.6 g, 0.10 mole) and trifluoromethanesulfuric acid (150.0 g, 1.0 mole). Although analysis of several samples of the gas phase indicated about 80% selectivity to propane, the ethylene content of the gas phase was very low (i.e. 1.8 - 4.9 wt. % — since most of the olefin was absorbed into the acid where it underwent undesirable side reactions. Therefore, only a small amount of the ethylene feed actually participated in the desired alkylation reaction.

What is claimed is:

1. An alkylation process wherein a paraffinic hydrocarbon feedstock comprising a component selected from the group consisting of methane, ethane, propane, n-butane and mixtures thereof, is alkylated under substantially anhydrous alkylation conditions with a C$_2$-C$_5$ olefin in the presence of a substantially liquid phase catalyst comprising (a) one or more Lewis acids selected from the group consisting of the fluorides, chlorides and bromides of vanadium, niobium, tantalum, chromium, molybdenum, tungsten, arsenic, antimony, phosphorus, bismuth and the chlorides and bromides of gallium and (b) a hydrogen halide, wherein the hydrogen halide is hydrogen fluoride, hydrogen chloride or hydrogen bromide, the molar ratio of said hydrogen halide to said Lewis acid ranging between 1:1 and about 100:1, and forming an alkylate having an average molecular weight greater than that of the feedstock.

2. The process of claim 1 wherein said Lewis acid is selected from the group consisting of tantalum pentafluoride, niobium pentafluoride and mixtures thereof and the hydrogen halide is hydrogen fluoride.

3. The process of claim 1 wherein said Lewis acid is phosphorus pentafluoride and the hydrogen halide is hydrogen fluoride.

4. The process of claim 1 wherein said molar ratio ranges between 2:1 and about 75:1.

5. The process of claim 1 wherein the molar ratio of olefin to paraffin ranges from 1:1 to 1:200.

6. The process of claim 1 wherein said paraffinic hydrocarbon feedstock comprises a component selected from the group consisting of methane, ethane, propane and mixtures thereof.

7. The process of claim 1 wherein said paraffinic hydrocarbon feedstock comprises a component selected from the group consisting of methane, ethane and mixtures thereof.

8. The process of claim 1 wherein said paraffinic hydrocarbon feedstock comprises methane.

9. The process of claim 1 wherein said alkylation is conducted in the substantial absence of aromatic compounds.

10. The process of claim 1 wherein the olefin comprises a component selected from the group consisting of ethylene, propylene and mixtures thereof.

11. An alkylation process wherein a paraffinic hydrocarbon feedstock comprising a component selected from the group consisting of methane, ethane, propane, n-butane and mixtures thereof is alkylated at a temperature ranging between about $-100°$ and $+150°$ C. and under substantially anhydrous conditions with a $C_2-C_5$ olefin in the presence of a substantially liquid phase catalyst comprising (a) a metal fluoride wherein the metal is a Group VB metal and (b) hydrogen fluoride, the molar ratio of hydrogen fluoride to metal fluoride ranging between 1:1 and about 100:1 so as to form an alkylate having an average molecular weight greater than that of the feedstock.

12. The process of claim 11 wherein the molar ratio of olefin to paraffin ranges from 1:3 to 1:50.

13. The process of claim 11 wherein the amount of olefin contacted with the catalyst ranges from about 0.0001 to about 0.05 parts by volume of olefin per part by volume of catalyst passing the point of olefin introduction.

14. The process of claim 11 wherein the volume percent of catalyst in the liquid hydrocarbon plus catalyst ranges from about 30 to about 85.

15. The process of claim 11 wherein said paraffinic hydrocarbon feedstock comprises a component selected from the group consisting of methane, ethane, propane and mixtures thereof.

16. The process of claim 11 wherein said paraffinic hydrocarbon feedstock comprises methane.

17. The process of claim 11 wherein said alkylation is conducted in the presence of hydrogen.

18. The process of claim 11 wherein the olefin comprises a component selected from the group consisting of ethylene, propylene and mixtures thereof.

19. An alkylation process wherein a paraffinic hydrocarbon feedstock comprising a component selected from the group consisting of methane, ethane, propane, n-butane and mixtures thereof, is alkylated at a temperature between about $-30°$ and $+100°$ C. and under substantially anhydrous conditions with a $C_2-C_5$ olefin in the presence of a catalyst comprising (a) a metal fluoride selected from the group consisting of tantalum pentafluoride, niobium pentafluoride and mixtures thereof and (b) hydrogen fluoride, the molar ratio of hydrogen fluoride to metal fluoride ranging between 1:1 and about 100:1, thereby forming an alkylate containing $C_3-C_7$ branched paraffins.

20. The process of claim 19 wherein said alkylation occurs in the substantial absence of aromatic compounds.

21. The process of claim 19 wherein the molar ratio of hydrogen fluoride to metal fluoride ranges between 2:1 and about 75:1.

22. The process of claim 19 wherein the paraffins so formed are further contacted with the catalyst for a period of time sufficient to form an olefin having the same number of carbon atoms as the corresponding paraffin.

23. The process of claim 22 wherein the olefin so formed undergoes further alkylation with a $C_1-nC_4$ paraffin.

24. The process of claim 22 wherein the olefin so formed undergoes further alkylation with a $C_1-C_3$ paraffin.

25. The process of claim 19 wherein said olefin comprises a component selected from the group consisting of ethylene, propylene and mixtures thereof.

26. The process of claim 19 wherein said paraffinic hydrocarbon feedstock comprises a component selected from the group consisting of methane, ethane, propane and mixtures thereof.

27. The process of claim 19 wherein said paraffinic hydrocarbon feedstock comprises a component selected from the group consisting of methane, propane and mixtures thereof.

28. The process of claim 19 wherein said paraffinic hydrocarbon feedstock comprises methane.

* * * * *